(12) United States Patent
Lee et al.

(10) Patent No.: US 7,906,317 B2
(45) Date of Patent: Mar. 15, 2011

(54) APPARATUS FOR THIN-LAYER CELL SMEAR PREPARATION AND IN-SITU HYBRIDIZATION

(75) Inventors: Bor-Heng Lee, Yilan County (TW); Chiu-Cho Yan, Kaohsiung County (TW); Ying-Chih Wang, Yilan County (TW); Ching-Yu Lin, Yilan County (TW)

(73) Assignee: King Car Food Industrial Co., Ltd., Taipei (TW)

( * ) Notice: Subject to any disclaimer, the term of this patent is extended or adjusted under 35 U.S.C. 154(b) by 811 days.

(21) Appl. No.: 11/875,940

(22) Filed: Oct. 21, 2007

(65) Prior Publication Data
US 2009/0104686 A1 Apr. 23, 2009

(51) Int. Cl.
C12M 1/34 (2006.01)
C12M 1/00 (2006.01)
C12M 1/26 (2006.01)
C12M 3/00 (2006.01)
A61B 10/00 (2006.01)
A61B 1/66 (2006.01)

(52) U.S. Cl. ............ 435/287.1; 435/287.2; 435/307.1; 435/309.1; 435/803; 435/805; 600/172; 600/562; 600/569; 600/572

(58) Field of Classification Search ........... 435/287.1, 435/287.2, 307.1, 309.1, 803, 805; 600/172, 600/562, 569, 572
See application file for complete search history.

(56) References Cited

U.S. PATENT DOCUMENTS

| | | | |
|---|---|---|---|
| 6,436,662 B1 * | 8/2002 | Mielzynska et al. | 435/40.5 |
| 2002/0039796 A1 * | 4/2002 | Dores et al. | 436/177 |
| 2003/0021021 A1 * | 1/2003 | Branch | 359/396 |

* cited by examiner

*Primary Examiner* — Michael A Marcheschi
*Assistant Examiner* — Robert Warden
(74) *Attorney, Agent, or Firm* — WPAT, PC; Justin King

(57) ABSTRACT

The present invention discloses an apparatus for thin-layer cell smear preparation and in-situ hybridization, comprising at least one positioning device and a sealing device. The positioning device comprises at least one first opening. When the positioning device is set on a carrier device, the wall of the first opening and the carrier device form a cavity. The cavity is used to accommodate a cell suspension. The sealing device is provided on the positioning device for sealing the cavity to form an enclosed space.

11 Claims, 3 Drawing Sheets

APPARATUS FOR THIN-LAYER CELL SMEAR PREPARATION AND IN-SITU HYBRIDIZATION

BACKGROUND OF THE INVENTION

1. Field of the Invention

The present invention is generally related to an apparatus for thin-layer cell smear preparation and in-situ hybridization, and more particularly to an apparatus for cell smear preparation and in-situ hybridization to prepare a thin-layer cell smear and carry out in-situ hybridization.

2. Description of the Prior Art

At present, a cervical smear is a major method for cervical cancer prophylaxis. The conventional cervical smear examination uses a cytology spatula or brush to collect cervical cells and coats on a slide for pathological diagnosis in a laboratory. Although the accuracy is not high enough, almost all of the gynecologist-obstetricians agree that the cervical smear examination should be done every year and no problem for three consecutive years can be generally considered as safe from the cervical cancer.

The cervical smear examination has been practiced for years. The controversial point in medicine is that the false negative result is as high as 10~40%. Some is caused by poor sampling technique while some is caused by the examinee, such as cervical atresia, cervical atrophy without hormone replacement therapy after menopause, and serious anteflexion or retroflexion of uterus, to make sampling difficult.

On the other hand, if the specimen cells on the smear are too thick, that is, many layers of cells are overlapped, the diagnosis becomes difficult. This can be improved by enhancing the training of medical staff.

In addition, the common false negative result is caused by misdiagnosis. Since typically there are two or three hundred thousand cells on a smear, it is difficult to make the diagnosis in a few minutes. Therefore, firstly screening the normal smears by cell technicians is carried out and then the rest of smears, about 10~20% of smears, are left to be diagnosed by doctors.

In recent years, in order to increase the smear accuracy, many auxiliary screening methods, such as thin-layer cell smear ThinPrep™ and SurePath™, etc., have been developed continually in medicine. In the thin-layer cell smear, a cytology spatula or brush is used to collect cervical cells and placed in a special preservation solution and after stirred to become uniform, the smear with uniform distribution of cells is prepared for observation. The thin-layer smear has uniform distribution of the specimen cells thereon and thus does not cause the phenomenon of cell overlapping so as to increase the detection rate. In addition, cells are concentrated in a relatively small area for easy diagnosis. Therefore, the errors can be reduced and the accuracy is higher than the conventional cervical smear, about 70~95%.

The factors to cause cervical cancer are numerous. Infection of human papillomaviruses (HPV) is the most important factor. Almost all of the cervical cancers are caused by HPV. U.S. food and drug administration approved in April, 2003 that women with the age over 30 having the cervical smear examination can also choose to have the HPV DNA examination. That is, the cervical specimen cells can be examined to find the existence of HPV DNA, besides abnormal appearance.

In-situ hybridization (ISH) or fluorescence in-situ hybridization (FISH) fixes cells on a slide, destroys cell membranes, and uses a probe under a proper condition to perform hybridization in the cells. The probe uses biotin to label or directly labels fluorescence to have different colors or fluorescence and then a microscope is used to have final diagnosis. Using in-situ hybridization technique to detect HPV dose not require amplification by polymerase chain reaction (PCR). In addition, the pathological staining result and molecular detection reaction can be integrated to provide the individual cell detection result of cells on each smear. Thus, clinicians have further information for diagnosis. Besides detecting virus infection, whether the HPV virus gene inserts into the cell chromatin or not can be recognized. It is an important factor in cytopathic effect.

In the prior art, the in-situ hybridization detection by the thin-layer cell smear has to use the apparatus, that is come together with ThinPrep™ or SurePath™, to prepare the thin-layer cell smear specimen. Then, the device, such as the hybridization frame or hybridization chamber, required to perform the in-situ hybridization experiment is attached on a slide to perform the subsequent reaction, such as hybridization. These operations are tedious and the labor and material costs are high.

SUMMARY OF THE INVENTION

In light of the above background about inconvenience and disadvantages, in order to fulfill the requirements of the industry, the present invention provides an apparatus for thin-layer cell smear preparation and in-situ hybridization to solve the target that can not be achieved by the cell smear apparatus in the prior art.

One object of the present invention is to provide an apparatus for thin-layer cell smear preparation and in-situ hybridization to simplify the thin-layer cell smear preparation and operations for the in-situ hybridization experiment by integrating two functions in one apparatus.

Accordingly, the present invention discloses an apparatus for thin-layer cell smear preparation and in-situ hybridization. The apparatus for thin-layer cell smear preparation and in-situ hybridization is used to prepare the thin-layer cell smear and perform in-situ hybridization. The apparatus comprises one positioning device and a sealing device. The positioning device is provided on a carrier device and comprises at least one opening. The wall of the opening and the carrier device form a cavity. By having the cross-linking agent in the bottom of the cavity adsorb the cells in the cell suspension, a thin-layer cell smear is formed. The sealing device is provided on the positioning device for sealing the cavity to form an enclosed space. The enclosed space is used to carry out in-situ hybridization.

DESCRIPTION OF THE PREFERRED EMBODIMENTS

According to the above objects, the present invention discloses an apparatus for thin-layer cell smear preparation and in-situ hybridization, which is an experimental apparatus to integrate two experiments, preparing the thin-layer cell smear and performing in-situ hybridization, in one apparatus. What is probed into the invention is a novel apparatus to simplify the thin-layer cell smear preparation and operations for the in-situ hybridization experiment by integrating two functions in one apparatus. Detail descriptions of the steps and compositions will be provided in the following in order to make the invention thoroughly understood. Obviously, the application of the invention is not confined to specific details familiar to those who are skilled in the art. On the other hand, the common compositions or steps that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1A:
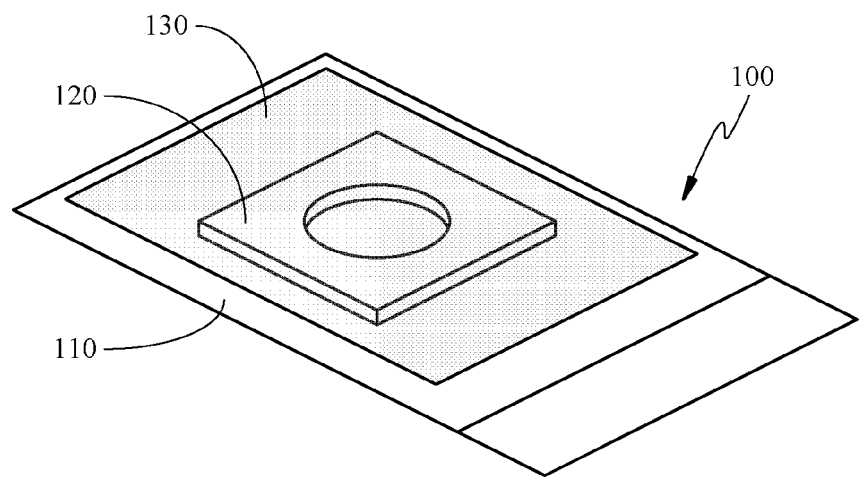
FIG. 1A is a schematic diagram illustrating the appearance of the apparatus for thin-layer cell smear preparation and in-situ hybridization according to the present invention.

As shown in FIG. 1A, a first embodiment of the invention discloses an apparatus 100 for thin-layer cell smear preparation and in-situ hybridization, comprising a positioning device 120 and a sealing device 130. The positioning device 120 comprises at least one first opening. When the positioning device 120 is set on a carrier device 110, the wall of the first opening and the carrier device 110 form a cavity. The carrier device 110 is coated with a cross-linking agent. In a preferred example of this embodiment, the carrier device 110 is a slide. The cross-linking agent is selected from the group consisting of the following or any combination thereof: poly-L-lysine or silane. The cavity is used to accommodate a cell suspension. By having the cross-linking agent in the bottom of the cavity adsorb the cells in the cell suspension, a thin-layer cell smear is formed. The sealing device 130 is provided on the positioning device 120 for sealing the cavity to form an enclosed space. In the enclosed space, the in-situ hybridization is carried out.

Figure 1B:
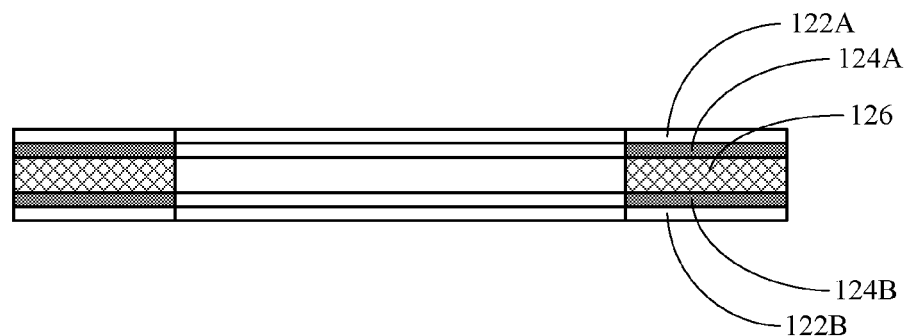
FIG. 1B is a schematic diagram illustrating the side view of the apparatus for thin-layer cell smear preparation and in-situ hybridization according to the present invention.
Figure 1C:
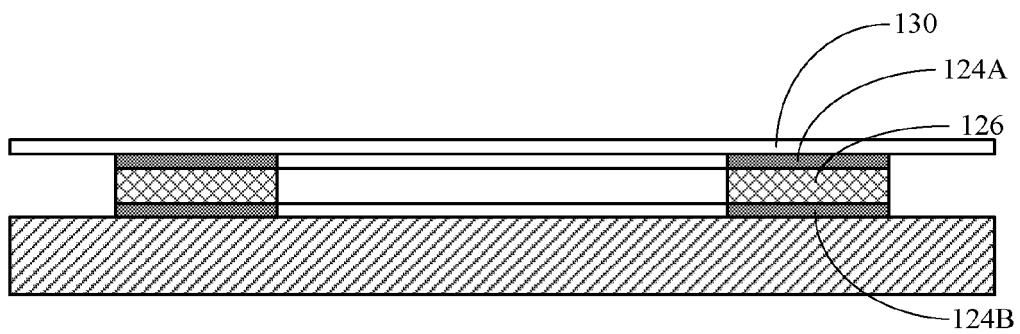
FIG. 1C is a schematic diagram illustrating the side view of the assembly of the carrier device and the apparatus for thin-layer cell smear preparation and in-situ hybridization according to the present invention.

As shown in FIG. 1B and FIG. 1C, the positioning device 120 comprises a structure with five layers. The five layers are, sequentially from top to bottom, a first release later 122A, a first adhesive layer 124A, a first matrix foam layer 126, a second adhesive layer 124B, and a second release layer 122B. The second release layer 122B is used to protect the second adhesive layer 124B. When the second release layer 122B is removed, the second adhesive layer 124B is adhered to the carrier device 110. Besides, the first release layer 122A is used to protect the first adhesive layer 124A. When the first release layer 122A is removed, the first adhesive layer 124A is adhered to the sealing device 130. The first matrix foam layer has a thickness of about 0.05 mm~5 mm. The material of the first matrix foam layer is selected from the group consisting of the following or any combination thereof: polyurethane (PU), polyvinylchloride (PVC), polyethylene (PE), polyethylene terephthalate (PET), and neoprene acrylic. The first adhesive layer and the second adhesive layer are made of acrylic adhesive.

Figure 2A:
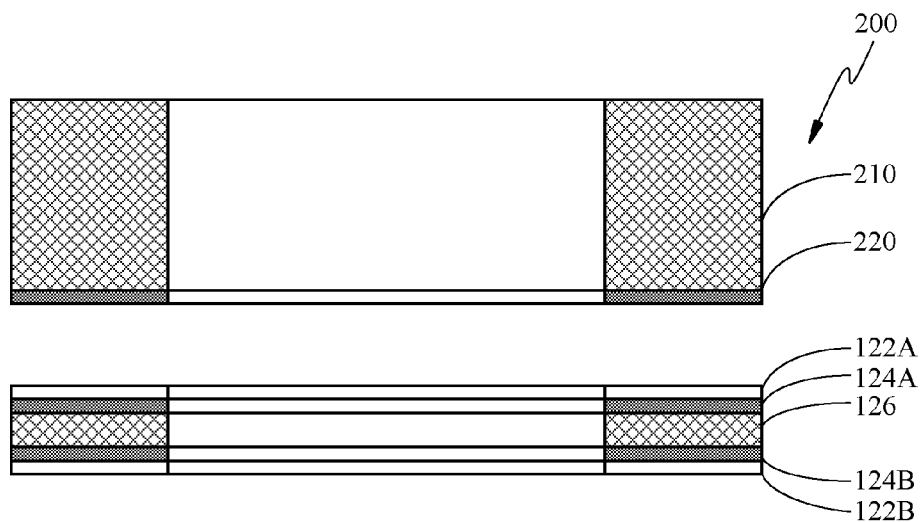
FIG. 2A is a schematic diagram illustrating the side view of the thickening device and the apparatus for thin-layer cell smear preparation and in-situ hybridization according to the present invention.
Figure 2B:
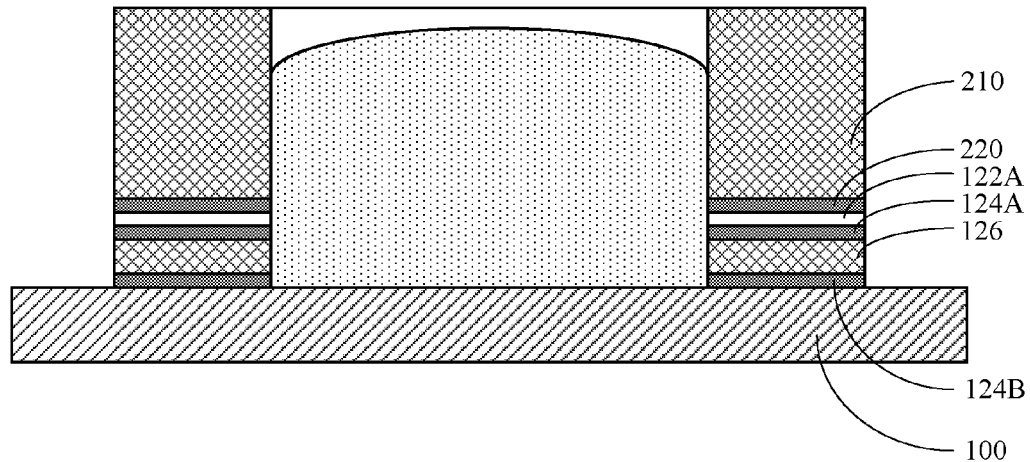
FIG. 2B is a schematic diagram illustrating the side view of the assembly of the thickening device and the apparatus for thin-layer cell smear preparation and in-situ hybridization according to the present invention.
Figure 2C:
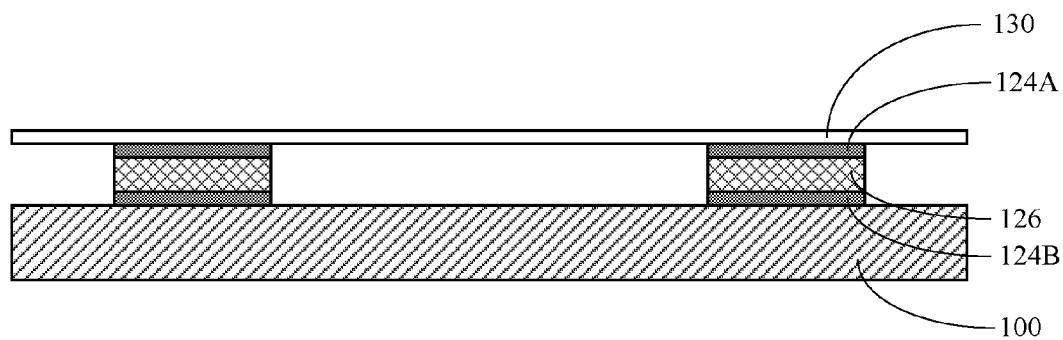
FIG. 2C is a schematic diagram illustrating the side view of the assembly of the carrier device and the apparatus for thin-layer cell smear preparation and in-situ hybridization according to the present invention.

As shown in FIGS. 2A, 2B, and 2C, another embodiment of the invention discloses an apparatus 100 for thin-layer cell smear preparation and in-situ hybridization, further comprising a thickening device 200. The thickening device 200 is provided on the positioning device 120 and comprises at least one second opening. When the thickening device 200 is coupled to the positioning device 120, the second opening is overlapped with the first opening. The thickening device 200 comprises a structure with two layers, a second matrix foam layer 210 and a third adhesive layer 220. The third adhesive layer 220 is adhered to the first release layer 122A. The second matrix foam layer has a thickness of about 0.05 mm~5 mm. The material of the second matrix foam layer is selected from the group consisting of the following or any combination thereof: polyurethane (PU), polyvinylchloride (PVC), polyethylene (PE), polyethylene terephthalate (PET), and neoprene acrylic.

The apparatus for thin-layer cell smear preparation and in-situ hybridization comprises three types. The first type is an apparatus having only a one-layer positioning device. The positioning device and the sealing device are coupled together on a carrier device to prepare the thin-layer cell smear and also perform in-situ hybridization. The second type is an apparatus having a multi-layer positioning device. By the multi-layer positioning device, the space to accommodate the cell suspension in the positioning device is increased. The third type is an apparatus further comprising a thickening device to achieve the purpose of increasing the space for accommodating the cell suspension. The thickness of the thickening device can be arbitrarily adjusted. The method to install the multi-layer positioning device and the thickening device includes two types: (1) before coupled with the carrier device, a multi-layer positioning device or a thickening device is used to increase the thickness; (2) after coupled with the carrier device, it is coupled with another positioning device or a thickening device to increase the thickness.

The invention discloses apparatus for thin-layer cell smear preparation and in-situ hybridization. The method for thin-layer cell smear preparation and in-situ hybridization comprises the following steps. At first the carrier device 110 is provided. Next, a coating procedure is performed. A cross-linking agent is coated on a surface of the carrier device. After the cross-linking agent is dried, the cavity is formed by setting the positioning device on the carrier device.

After the coating procedure is completed, specimen cells in the preservation solution are used to prepare a cell suspension and the cell suspension is added into the cavity. Then, a setting procedure is performed. By having the cross-linking agent adsorb the specimen cell precipitate in the cell suspension, the thin-layer cell smear is formed. Finally, an in-situ hybridization procedure is performed. By adding a probe and sealing the cavity by the sealing device 130, an enclosed space is formed to carry out the in-situ hybridization.

Figure 3A:
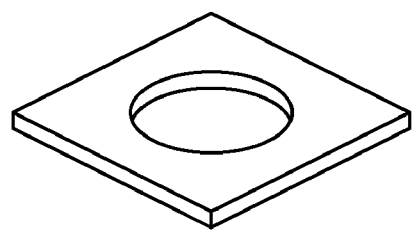
FIG. 3A is a schematic diagram illustrating the positioning device having one opening according to the present invention.
Figure 3B:
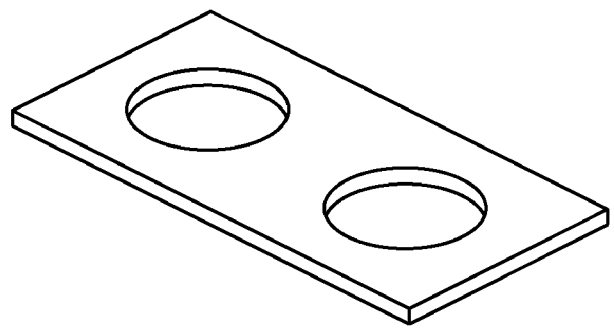
FIG. 3B is a schematic diagram illustrating the positioning device having two openings according to the present invention.
Figure 3C:
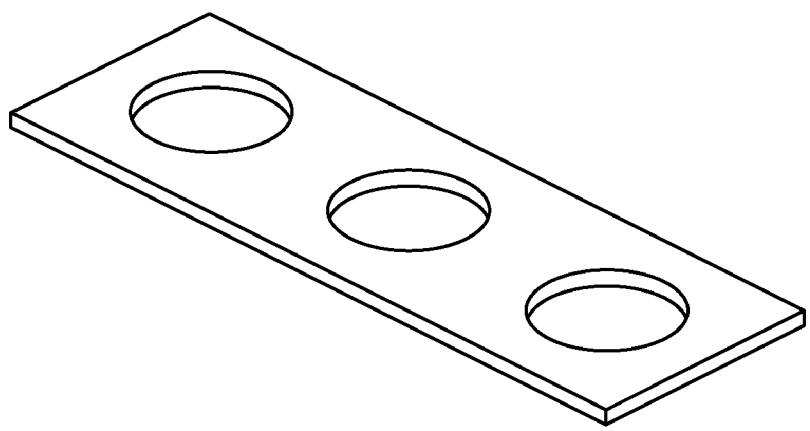
FIG. 3C is a schematic diagram illustrating the positioning device having three openings according to the present invention.

As shown in FIGS. 3A, 3B, and 3C, a preferred example of this embodiment is shown where the positioning device comprises at least one opening or a plurality of openings. Different detections can be carried out in different openings. The shape of the opening is selected from the group consisting of the following: circular, square, triangular, wedged or any geometrical shape. However, the invention is not limited to these examples.

Example 1

1. A slide (glass or plastic slide) is coated with a cross-linking agent, in order to have cells be adhered thereon. The slide is immersed in the poly-L-lysine or silane solution for 10 minutes and then taken out to dry at room temperature.

2. Specimen cells in the preservation solution or fixation solution is then centrifugal settling. After collected, the cells are then suspended in a buffer solution to prepare a cell suspension.

3. The release paper of the positioning device is removed and the positioning device is adhered to the slide. The cell suspension is added and set for 15 minutes to have the cells naturally precipitate and be adsorbed on the slide. Then, the cell suspension is poured out and the buffer solution is used to rinse once. It is stood to dry at room temperature.

A hybridization buffer solution comprising a fluorescence labeled nucleic acid probe is added. After the release paper is removed, it is sealed by the sealing device. At 37° C., the in-situ hybridization is carried out. After 4 hrs, the assembly of the positioning device and the sealing device is removed from the slide. The slide is washed by the 0.2×SSC buffer solution at 55° C. After washed by MQ, the slide is set to dry at room temperature to be observed by a fluorescence microscope.

Example 2

1. A slide (glass or plastic slide) is coated with a cross-linking agent, in order to have cells be adhered thereon. The slide is immersed in the poly-L-lysine or silane solution for 10 minutes and then taken out to dry at room temperature. The slide is assembled with the positioning device.

2. Specimen cells in the preservation solution or fixation solution is then centrifugal settling. After collected, the cells are then suspended in a buffer solution to prepare a cell suspension.

3. The release paper of the positioning device having the thickening device is removed and the positioning device is adhered to the slide. The cell suspension is added and set for 15 minutes to have the cells naturally precipitate and be adsorbed on the slide. Then, the cell suspension is poured out and the buffer solution is used to rinse once. It is stood to dry at room temperature.

4. The thickening device and the release paper of the positioning device are removed. A hybridization buffer solution comprising a fluorescence labeled nucleic acid probe is added. It is sealed by the sealing device and, at 37° C., the in-situ hybridization is carried out. After 4 hrs, the assembly of the positioning device and the sealing device is removed from the slide. The slide is washed by the 0.2×SSC buffer solution at 55° C. After washed by MQ, the slide is set to dry at room temperature to be observed by a fluorescence microscope.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An apparatus for thin-layer cell smear preparation and in-situ hybridization, the apparatus comprising:
   at least one positioning device, wherein said positioning device comprises a structure with five layers, sequentially from top to bottom, a first release layer, a first adhesive layer, a first matrix foam layer, a second adhesive layer, and a second release layer, wherein said positioning device further comprises at least one first opening wherein the wall of said first opening and a carrier device form a cavity when said positioning device is set on said carrier device and said cavity is for accommodating a cell suspension; and
   a sealing device provided on said positioning device for sealing said cavity to form an enclosed space.

2. The apparatus according to claim 1, wherein said second release layer is to protect said second adhesive layer and said second adhesive layer is adhered to said carrier device if said second release layer is removed.

3. The apparatus according to claim 1, wherein said first release layer is to protect said first adhesive layer and said first adhesive layer is adhered to said sealing device if said first release layer is removed.

4. The apparatus according to claim 1, wherein said first matrix foam layer has a thickness of about 0.05 mm-5 mm.

5. The apparatus according to claim 1, wherein said first matrix foam layer is selected from the group consisting of the following or any combination thereof: polyurethane (PU), polyvinylchloride (PVC), polyethylene (PE), polyethylene terephthalate (PET), and neoprene acrylic.

6. The apparatus according to claim 1, wherein said first adhesive layer and said second adhesive layer are made of acrylic adhesive.

7. The apparatus according to claim 1, further comprising: a thickening device provided on said positioning device and comprising at least one second opening wherein said second opening is overlapped with said first opening when said thickening device is coupled to said positioning device.

8. The apparatus according to claim 7, wherein said thickening device comprises a structure with two layers, a second matrix foam layer and a third adhesive layer, and said third adhesive layer is adhered to said first release layer.

9. The apparatus according to claim 8, wherein said second matrix foam layer has a thickness of about 0.05 mm~5 mm.

10. The apparatus according to claim 8, wherein said second matrix foam layer is selected from the group consisting of the following or any combination thereof: polyurethane (PU), polyvinylchloride (PVC), polyethylene (PE), polyethylene terephthalate (PET), and neoprene acrylic.

11. The apparatus according to claim 8, wherein said third adhesive layer is made of acrylic adhesive.

* * * * *